US006294340B1

United States Patent
Strittmatter et al.

(10) Patent No.: US 6,294,340 B1
(45) Date of Patent: *Sep. 25, 2001

(54) METHOD OF BINDING MATERIAL TO THE β-AMYLOID PEPTIDE

(75) Inventors: Warren J. Strittmatter; Allen D. Roses; David Huang, all of Durham, NC (US); Dmitry Y. Goldgaber, Setauket, NY (US)

(73) Assignee: Duke University, Durham, NC (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/734,490

(22) Filed: Oct. 21, 1996

Related U.S. Application Data

(63) Continuation of application No. 08/139,470, filed on Oct. 20, 1993, now abandoned.

(51) Int. Cl.[7] .................. G01N 33/53; G01N 33/543; G01N 33/563
(52) U.S. Cl. .................. 435/7.1; 435/7.8; 435/7.9; 435/7.95; 435/40.5; 436/512; 436/518; 436/536; 436/63; 436/804; 530/391.1; 530/810; 530/839
(58) Field of Search .................. 435/7.1, 7.8, 7.9, 435/7.95, 40.5; 436/518, 512, 536, 63, 804; 424/130.1, 178.1, 1.49; 530/387.1, 389.1, 391.1, 839

(56) References Cited

U.S. PATENT DOCUMENTS 4,271,140 * 6/1981 Bunting .
4,891,313 * 1/1990 Berger et al. .
5,593,846 * 1/1997 Schenk et al. .

FOREIGN PATENT DOCUMENTS

WO 91/16819  11/1991  (WO) ............... A01N/37/18
WO 92/03474   3/1992  (WO) ............... C07K/7/04

OTHER PUBLICATIONS

Adlersberg, 1976. The immunoglobulin hinge (interdomain) region. La Ricerca Clin. Lab. 6: 191–205.*
Thorpe (1993) Trends in Biotech. 11:40–42.*
Huang et al J. Neuoimmunol. (1993) 48 : 199–204.*
Ishii et al. (1976) Aeta Neuropath. (Beil.) 36:243–249.
Sigma Chemical Catalogue (1991), p. 1194.*
Goding (1983) "Monoclonal Antibodies" Academic Press, Orlando, pp. 118–125 and 75–87.*
Roitt (1991) "Essential Immunology", Blackwell Scientific Publications, Oxford, pp. 35–46.*
Yoshio Namba et al., Apolipoprotein E Immunoreactivity in cerebral amyloid deposits and neurofibrillary tangles in Alzheimer's disease and kuru plaque amyloid in Creutzfeldt–Jakob disease, *Brain Research* 541, 163–166 (1991).
T. Wisnicwski and Blas Frangione, Apolipoprotein E: a pathological chaperone protein in patients with cerebral and systemic amyloid, *Neuroscience Letters*, 135, 235–238 (1992).
Steven G. Younkin, Processing of the Alzheimer's Disease βA4 Amyloid Protein Precursor (APP), *Brain Pathology 1*, 253–262 (1991).
John A. Hardy and Gerald A. Higgins, Alzheimer's Disease: The Amyloid Cascade Hypothesis, *Science 256*, 184–185 (1992).
D. Burdick et al., Assembly and Aggregation Properties of Synthetic Alzheimer's A4/β Amyloid Peptide Analogs, *The Journal of Biological Chemistry 267*, 546–554 (1992).
K. Beyreuther and C. L. Masters, Amyloid Precursor Protein (APP) and βA4 Amyloid in the Etiology of Alzheimer's Disease: Precursor–Product Relationships in the Derangement of Neuronal Function, *Brain Pathology 1*, 241–251 (1991).
W.J. Strittmatter et al., Apolipoprotein E: High–avidity binding to β amyloid and increased frequency of type 4 allele in late–onset familial Alzheimer disease, *Proc. Natl. Acad. Sci. USA 90* 1977–1981 (1993).
C.J. Barrow and M.G. Zagorski, Solution Structures of β Peptide and Its Constituent Fragments: Relation to Amyloid Deposition, *Science 253*, 179–253 (1991).

* cited by examiner

Primary Examiner—Christopher L. Chin
Assistant Examiner—James L. Grun
(74) Attorney, Agent, or Firm—Myers Bigel Sibley & Sajovec

(57) ABSTRACT

The present invention relates to the finding that antibodies bind to the β-amyloid peptide, and that β-amyloid peptide binds the hinge region of the immunoglobulin heavy chain, thereby preserving the ability of the immunoglobulin to bind antigen. Methods for binding compounds such as detectable groups to β-amyloid peptide are accordingly presented.

12 Claims, 3 Drawing Sheets

METHOD OF BINDING MATERIAL TO THE β-AMYLOID PEPTIDE

This application is a continuation, of application Ser. No. 08/139,470, filed Oct. 20, 1993, now abandonded.

This work was supported by National Institutes of Health L.E.A.D. award 5R35 AG-07922 and National Institutes of Health Alzheimer's Disease Research Center 5P50 AG-05128. The Government has certain rights in this invention.

FIELD OF THE INVENTION

The present invention relates to Alzheimer's disease, and particularly relates to methods of binding antigenic compounds to the β-amyloid peptide found in the senile plaques of Alzheimer's disease.

BACKGROUND OF THE INVENTION

The senile amyloid plaques and congophilic angiopathic lesions found in abundance in brain of patients with Alzheimer's disease are abnormal extracellular structures. The biochemical composition of these structures has been extensively studied to better understand their possible role in the pathogenesis of this dementing disease. The mature amyloid plaque is a complex structure, consisting of a central core of amyloid fibrils surrounded by dystrophic neurites, axonal terminals and dendrites, microglia and fibrous astrocytes. The amyloid core of the senile amyloid plaque, and which surrounds blood vessels to produce the congophilic angiopathy, is a peptide of 39 to 43 amino acids termed the β-Amyloid (βA) peptide, the Aβ peptide, the A4 protein, or the βA4 peptide. βA peptide is found in the brain in Alzheimer's disease, Down's syndrome, hereditary cerebral hemorrhage of the Dutch type, and in old age. See, e.g., K. Kosik *Science* 256, 780–783 (1992).

E. Kline et al., PCT Appln WO 91/16819 describes a method of treating Alzheimer's disease by administering the β-amyloid peptide itself, or an active fragment thereof. H. Potter, PCT Appln WO 92/03474, describes a therapeutic method of treating individuals, such as Alzheimer's disease patients, to prevent the formation of an α-antichymotrypsin-β-amyloid peptide complex by administering to the subject a synthetic peptide comprising a fragment of the β-amyloid peptide.

The βA peptide is produced by the abnormal proteolytic processing of a larger protein, the amyloid precursor protein (APP). APP itself has been identified in the senile amyloid plaque, and additional proteins which have been localized to senile amyloid plaques and angiopathic lesions include apolipoprotein E, alpha-1-antichymotrypsin, complement factors C1q and C3q, APP, and IgG. See, e.g., W. Strittmatter et al., *Proc. Natl. Acad. Sci.* 90, 1977 (1993); Abraham et al., *Cell*, 52, 487 (1988), Eikelenboom et al., *Acta Neuropathol.*, 57, 239 (1982); McGeer et al., *Canad. J. Neuro. Sci.*, 16, 516 (1989), Beyreuther et al., *Brain Pathol.*, 1, 241 (1991); Ishii et al., *Acta Neuropathol.*, 36, 243 (1976). The mechanisms by which these proteins aggregate in the extracellular space to associate with the senile amyloid plaque and congophilic angiopathic lesion are not known. Hence, there is an ongoing need for new ways to investigate and combat this disorder.

SUMMARY OF THE INVENTION

Disclosed is a method of binding a compound to β-amyloid peptide. The method is based on the finding that the hinge region of antibodies bind to the β-amyloid peptide. The method comprises the steps of contacting a linker antibody having a hinge region (and preferably at least one antigen binding site) to the β-amyloid peptide so that the hinge region binds to the β-amyloid peptide. A compound to be delivered is bound to the antibody before, during, or after the contacting step. In a preferred embodiment the Fc receptor binding region of the linker antibody is deleted.

Where the compound to be delivered is an antigenic compound, the linker antibody is bound with the combining site free, the antibody is selected so that it specifically binds to the compound to be delivered at the combining site, and the antigenic compound is bound to the antigen binding site (before, concurrently with or after the contacting step) so that the antigenic compound is bound to the β-amyloid peptide.

The method is useful, among other things, for histologic and diagnostic examination of Alzheimer's disease brain tissue, or brain tissue of a patient suspected of being afflicted with Alzheimer's disease, both in vitro and in vivo.

The foregoing and other objects and aspects of the present invention are explained in detail in the specification set forth below.

BRIEF DESCRIPTION OF THE DRAWINGS

FIG. 2B shows binding of affinity purified CSF IgG to $βA_{(1-28)}$ peptide following various washes. CSF, which contains IgG, was incubated with either $βA_{(1-28)}$ or ethanolamine previously immobilized to Immobilon AV discs, and then trailed as described for FIG. 2a.

(without cerebrospinal fluid) were incubated with the Immobilon AV membrane discs. The membranes were washed in PBS and 6M guanidine, and retained proteins were eluted by boiling in Laemmli buffer. After electrophoresis and Western transfer, albumin was detected with the anti-albumin antibody.

Figure 5:
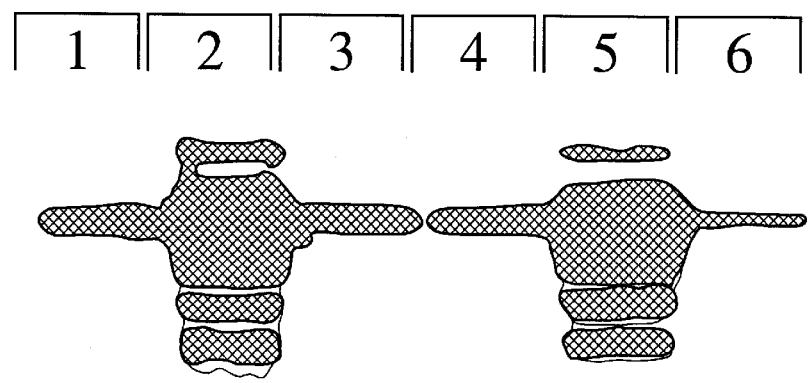

FIG. 5 shows binding of CSF albumin to immobilized $\beta A_{(1-28)}$ (Lanes 1 and 4); to anti-albumin IgG previously bound to immobilized $\beta A_{(1-28)}$ (Lanes 2 and 5); or to anti-ferritin IgG previously bound to immobilized $\beta A$ (Lanes 3 and 6). Anti-albumin IgG or anti-ferritin IgG was incubated with $\beta A$ peptide immobilized to Immobilon AV discs, and the discs washed with PBS. The discs were then incubated with cerebrospinal fluid, and washed with PBS (Lanes 1,2,3) or with PBS and 6 M guanidine hydrochloride (Lanes 4,5,6). Proteins retained by each membrane were then eluted by boiling in Laemmli buffer, and albumin was detected with anti-albumin antibody after electrophoresis and Western transfer.

DETAILED DESCRIPTION OF THE INVENTION

To study the binding of various proteins to the $\beta A$ peptide, the present inventors used a previously developed in vitro assay in which $\beta A$ peptide, or fragments thereof, are covalently immobilized to a membrane matrix. See Strittmatter et al., *Proc. Natl. Acad. Sci.* 90, 1977 (1993). Using this assay the binding of apolipoprotein E and amyloid precursor protein (APP) to synthetic $\beta A$ peptide has been previously characterized (Strittmatter et al., *Proc. Natl. Acad. Sci.* 90, 1977 (1993); Strittmatter et al., *Exper. Neurol.* 122, 327 (1993).

The present invention is based on the findings that (1) IgG directly and avidly binds $\beta A$ amyloid, (2) it is the domain between amino acids 12–28 of $\beta A$ that binds IgG, and (3) $\beta A$ peptide binds the hinge region of the immunoglobulin heavy chain, thereby preserving the ability of the immunoglobulin to bind antigen. The term "hinge region" is used herein to indicate the area of the heavy chain of the immunoglobulin G molecule which lies between the first and second constant region domains (CH1 and CH2). See, e.g., Goodman, *Immunoglobulin Structure and Function*, In: Stites and Terr (Eds.), *Basic and Clinical Immunology*, 7th ed., 1991, Appleton & Lange, p. 110. The binding of IgG and $\beta A$ was found to resist dissociation by either sodium dodecyl sulfate or guanidine hydrochloride. These findings indicate that proteins which do not directly bind to $\beta A$ peptide may nonetheless become bound to the senile amyloid plaque and the angiopathic lesion by interaction with IgG.

The senile amyloid plaque and congophilic angiopathic lesion are complex structures containing many proteins; the recruitment of proteins via the IgG-$\beta A$ peptide link may be important in the pathogenesis of the disease. The amyloid cascade hypothesis, discussed by Hardy & Higgins, *Science*, 256, 184 (1992), posits that deposition of amyloid $\beta$ protein is the causative agent of Alzheimer's pathology and that the neurofibrillary tangles, cell loss, vascular damage, and dementia follow as a direct result of this deposition. The binding of IgG to $\beta A$ provides a sandwich mechanism for the deposition of other plaque constituents in Alzheimer's disease.

As used herein, the term "amyloid plaque" or "senile plaque" refers to the extracellular amyloid deposits that are a characteristic feature of Alzheimer's disease, and which consist of a central core of amyloid fibrils surrounded by dystrophic neurites, axonal terminals and dendrites, microglia and fibrous astrocytes. See D. Selkoe *Neuron* 6, 487–498 (1991). The amyloid plaque surrounds blood vessels to produce the congophilic angiopathy found in Alzheimer's disease.

The finding that IgG is capable of binding both its specific antigen and $\beta A$ peptide presents a mechanism by which proteins which do not directly bind $\beta A$ can be bound to these structures via IgG, and provides a method to detectably label the pathological lesions found in Alzheimer's disease. Such labelling may be used in staining anatomical specimens and in detecting pathological lesion in situ. In general, the present invention provides a means for delivering or binding an antigenic compound to the $\beta A$ peptide for any purpose, whether therapeutic or diagnostic.

Any antibody may be employed in carrying out the present invention so long as it has a hinge region capable of binding to the $\beta A$ peptide. The terms "antibody" and "antibodies" as used herein refers to all types of immunoglobulins, including IgG, IgM, IgA, IgD, and IgE, including the fragments thereof. The term "immunoglobulin" includes the subtypes of these immunoglobulins, such as $IgG_1$, $IgG_2$, $IgG_3$, $IgG_4$, etc. Of these immunoglobulins, IgM and IgG are preferred, and IgG is particularly preferred. The antibodies may be of any species of origin, including (for example) mouse, rat, rabbit, horse, or human, or may be chimeric antibodies. See, e.g., M. Walker et al., *Molec. Immunol.* 26, 403–11 (1989). The antibodies may be monoclonal antibodies. Such monoclonal antibodies are produced in accordance with known techniques. The term "antibody" as used herein includes antibody fragments which retain the capability of binding to a target antigen, for example, $F(ab')_2$ fragments, and the corresponding fragments obtained from antibodies other than IgG, retain a hinge region and may be used in the present invention. Such fragments are also produced by known techniques.

The monoclonal antibodies may be recombinant monoclonal antibodies produced according to the methods disclosed in Reading U.S. Pat. No. 4,474,893, or Cabilly et al., U.S. Pat. No. 4,816,567. The antibodies may also be chemically constructed by specific antibodies made according to the method disclosed in Segel et al., U.S. Pat. No. 4,676,980 (Applicants specifically intend that the disclosure of all U.S. patent references cited herein be incorporated herein by reference).

Monoclonal antibodies may be chimeric antibodies produced in accordance with known techniques. For example, chimeric monoclonal antibodies may be complementarity determining region-grafted antibodies (or "CDR-grafted antibodies"), or "humanized" antibodies produced in accordance with known techniques. See, e.g., H. Waldmann, PCT Application WO 93/01289; M. Clark, PCT Application WO 92/16562; M. Bendig et al., PCT Application WO 92/15683; K. Tan, PCT Application WO 92/15699.

As used herein, the term "antigen-binding portion of an antibody" means the portion of the antibody that binds an antigen to which the antibody is specific. A preferred embodiment of this method comprises using a fragment of IgG having the $F_c$ region deleted, such as the $F(ab)'_2$ fragment.

Where it is desired to bind a compound which is not antigenic to the antibody to bind that compound to the $\beta A$ peptide, that compound may be bound to the antibody by direct means (e.g., covalently) or indirect means (e.g., via a chelator) by any suitable technique, such as the Iodogen method or with N-succinimidyl-3-(tri-n-butylstanyl) benzoate (the "ATE method"), as will be apparent to those skilled in the art. See, e.g., M. Zalutsky and A. Narula, *Appl. Radiat. Isot.* 38, 1051 (1987).

The compound to be bound to the 6A peptide may be a detectable group. Suitable detectable groups include, for example, radiolabels (e.g., $^{35}$S, $^{125}$I, $^{131}$I), enzyme labels (e.g., horseradish peroxidase, alkaline phosphates), and fluorescent labels (e.g., fluorescein) as used in accordance with known techniques.

Linker antibodies used to carry out the present invention, with or without the compound to be delivered bound thereto, may be provided in lyophylized form in a sterile aseptic container or may be provided in a pharmaceutical formulation, such as in combination with a pharmaceutically acceptable carrier such as sterile pyrogen-free water or sterile pyrogen-free physiological saline solution.

The step of contacting the linker antibody to the β-amyloid peptide may be carried out by any suitable means. The β-amyloid peptide may reside in nerve tissue and the contacting step is carried out in nerve tissue. The nerve tissue may or may not reside in a patient, depending upon whether the method is being carried out for histologic, diagnostic, or thereapeutic purposes. Where the technique is carried out on a tissue sample for histologic purposes (e.g., staining of the congophilic angiopathy), it may be carried out by contacting the tissue to a solution, typically an aqueous solution, containing the antibody (e.g., by washing the tissue with the solution or by immersing the tissue in the solution).

The step of binding the compound to be delivered to the antibody may be carried out before, during (i.e. concurrently with), or after the step of contacting the antibody to the β-amyloid peptide as described above. The binding step may be carried out by any of the means for carrying out the contacting step as described above.

For administration to a subject, the antibody will generally be mixed, prior to administration, with a non-toxic, pharmaceutically acceptable carrier substance (e.g. normal saline or phosphate-buffered saline), and will be administered using any appropriate procedure, e.g., intravenous or intra-arterial administration, injection into the cerebrospinal fluid). In addition, either intrathecal administration or injection into the carotid artery are advantageous for therapy of tumors located in the brain.

Dosage of the antibody will depend, among other things, on the route of administration, the nature of the compound being bound to the βA peptide, etc. For example, the dosage will typically be about 1 to 10 micrograms per Kilogram subject body weight.

The mechanism by which the hinge region of IgG binds βA peptide also presents the opportunity to devise methods to specifically and selectively block this interaction, and methods to deliver therapeutic molecules to the amyloid plaque. A therapeutic protein molecule is delivered to the amyloid plaque by raising IgG specific for the therapeutic molecule, then binding the therapeutic molecule to the immunoglobulin (or a fragment thereof) and delivering this construct to the area of pathological βA peptide deposition. Alternatively, the immunoglobulin could first be contacted to the βA peptide and then exposed to the therapeutic molecule, or these steps may be carried out concurrently. Conjugates of IgG and therapeutic protein molecules may be made using a variety of bifunctional protein coupling agents as are known in the art.

The present invention is also useful for blocking the pathological deposition of proteins which bind to β-amyloid peptide via IgG, providing a method of combatting diseases in which abnormal protein deposition on βA peptide occurs. Such a method would involve inhibiting the binding of IgG to βA peptide by contacting to the βA peptide a fragment of IgG capable of binding to the βA peptide but incapable of binding other proteins, for example, a fragment of IgG comprising the hinge region, but lacking the antigen-binding portion of the antibody.

The present invention also provides a method to screen compounds for the ability to block the IgG-βA peptide interaction. Generally, a screening method involves providing an aqueous solution containing βA peptide or a fragment thereof, adding to this aqueous solution a test compound suspected of inhibiting IgG binding, then adding IgG to the aqueous solution, and then detecting the presence of absence of bound IgG. Another embodiment of this method would utilize a βA peptide construct immobilized on a solid support, as described above (see Strittmatter et al., *Proc. Natl. Acad. Sci.* 90, 1977 (1993); also disclosed in co-pending patent application Ser. No. 07/959,251, filed Oct. 13, 1992). Detection of bound IgG may be carried out using antibodies with detection groups attached or by any suitable means, such as staining, affinity binding, competitive binding assay, etc., as are known in the art. The β-amyloid peptide fragment used in the in vitro assays described above could comprise $βA_{(1-28)}$ or $βA_{(12-28)}$, although other fragments that bind IgG may also be employed.

The following examples are provided to illustrate the present invention, and should not be construed as limiting thereof. In these examples, PBS means phosphate buffered saline; CSF means cerebrospinal fluid; SDS means sodium dedecyl sulfate; M means molar; mM means millimolar; mg means milligram; μg means microgram; ng means nanogram; ml means milliliter; μl means microliter; and °C. means degrees Centigrade.

EXAMPLE 1

MATERIALS AND METHODS

Affinity purified human IgG and IgG fragments (Fab, Fc, and F(ab)'$_2$) were purchased from Cappel-Organon Teknika, Durham, N.C. Peroxidase-conjugated goat antibodies to human IgG (heavy and light chains) were purchased from Pierce, Rockford, Ill. Sheep anti-human serum albumin (HSA) IgG, sheep anti-ferritin IgG, and peroxidase-conjugated sheep IgG against human serum albumin were purchased from The Binding Site, Ltd., San Diego, Calif. βA peptides ($βA_{(1-40)}$, $βA_{(1-28)}$, and $βA_{(12-28)}$ were obtained from Bachem, Torrance, Calif., US. The synthesis of peptides E.H. ("even-hydro", as explained below) and H.M. ("hydro-mimic" as explained below) have been described previously (Strittmatter et al., *Proc. Natl. Acad. Sci.* 90, 1977 (1993)). Human cerebrospinal fluid (CSF), from diagnostic lumbar punctures was obtained from the Kathleen Bryan Brain Bank at Duke University Medical Center, Durham, NC.

βA peptides, other peptides, or ethanolamine were covalently bound to 13 mm Immobilon AV affinity membrane (Millipore) discs as described previously, with 100 μg peptide. Strittmatter et al., *Proc. Natl. Acad. Sci.* 90, 1977 (1993). The membrane is a chemically activated hydrophilic microporous membrane which covalently immobilizes peptides and proteins through amino and thiol groups.

EXAMPLE 2

Binding of IgG to Immobilized Peptides

To characterize the binding of immunoglobulins to selected immobilized peptides, affinity-purified human IgG (0.3 ng), Fab (0.45 ng), Fc (0.15 ng) or F(ab)'$_2$ (0.45 ng) in 150 µl PBS, pH 7.4, were incubated with immobilized µA$_{(1-28)}$ peptide, other peptides, or with ethanolamine at room temperature for 30 minutes. The membranes were washed in a Millex filter holder (Millipore) with 3.0 ml PBS, followed by 700 µl 10% sodium dodecyl sulfate (SDS). Retained proteins were then eluted from the membranes by boiling five minutes in 150 µl Laemmli with β-mercaptoethanol. 45 µl of each sample was loaded on a 12% polyacrylamide gel. Electrophoresis and Western transfer were performed as previously described (Strittmatter et al., *Proc. Natl. Acad. Sci.* 90, 1977 (1993)). The Western transfer membrane was blocked with 40 ml Blotto (5% dried milk in Tris buffered saline pH 7.6) with 0.1% Tween 20 at room temperature for one hour. The membrane was incubated with peroxidase-conjugated goat anti-human IgG antibody which recognizes both heavy and light chains (diluted 1:4000 in Blotto) at 4° C. overnight. The membrane was rinsed four times with 20 ml Blotto and was then washed three times with 40 ml Blotto for five minutes. Antibody was visualized using an enhanced chemoluminescence detection kit (Amersham) and exposure of the membrane to Hyperfilm (Amersham), as described previously (Strittmatter et al., *Proc. Natl. Acad. Sci.* 90, 1977 (1993)).

Figure 1:
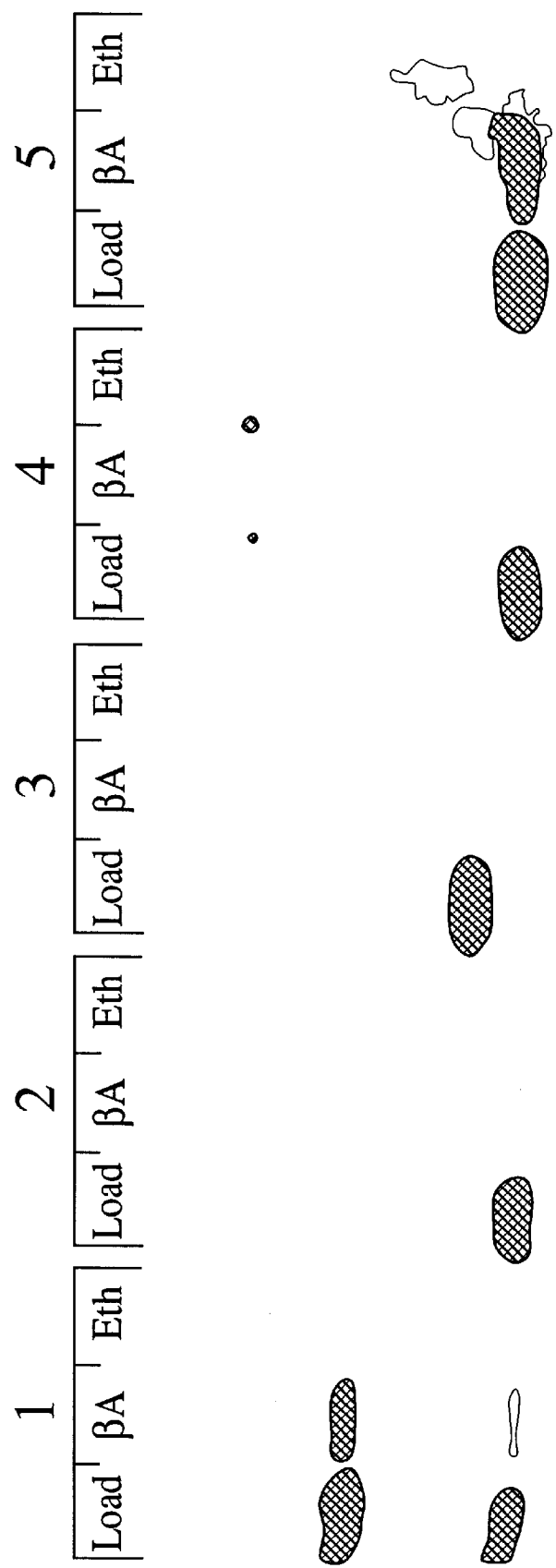
FIG. 1 shows binding of IgG and IgG domains to immobilized $βA_{(1-28)}$ and to immobilized ethanolamine. Panel 1: Affinity-purified IgG; Panel 2: Fab; Panel 3: $F_c$; Panel 4: Fab; Panel 5: $F(ab)'_2$. IgG and IgG domains were applied directly to a polyacrylamide gel (Load), or were incubated with $βA_{(1-28)}$ or with ethanolamine (Eth) previously immobilized to Immobilon AV membrane discs. The membranes were then washed with PBS and guanidine hydrochloride, then boiled in Laemmli buffer, and the eluted proteins electrophoresed, transferred to Immobilon P, and visualized as described.
Figure 2A:
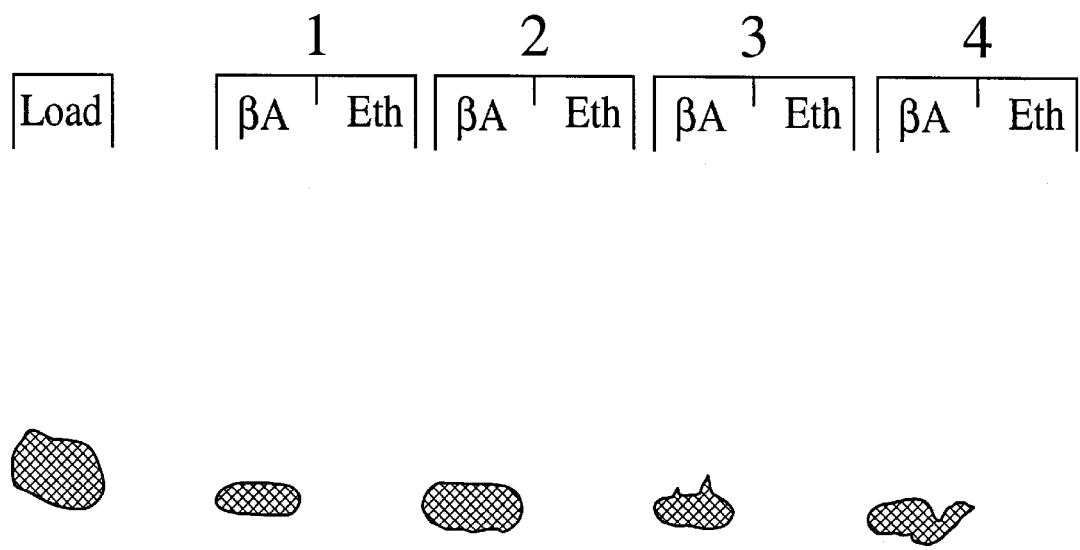
FIG. 2A shows binding of affinity purified $F(ab)'_2$ to $βA_{(1-28)}$ peptide following various washes. Affinity-purified $F(ab)'_2$ was incubated with either $βA_{(1-28)}$ or ethanolamine previously immobilized to Immobilon AV membrane discs. The membranes were then washed with 3.0 ml PBS (Panel 1), followed by 700 μl 5% SDS (Panel 2), 700 μl 4 M urea (Panel 3), or 6 M guanidine hydrochloride (Panel 4). Proteins were then eluted by boiling in Laemmli buffer, electrophoresed, and immunoglobulin visualized as described.
Figure 2B:
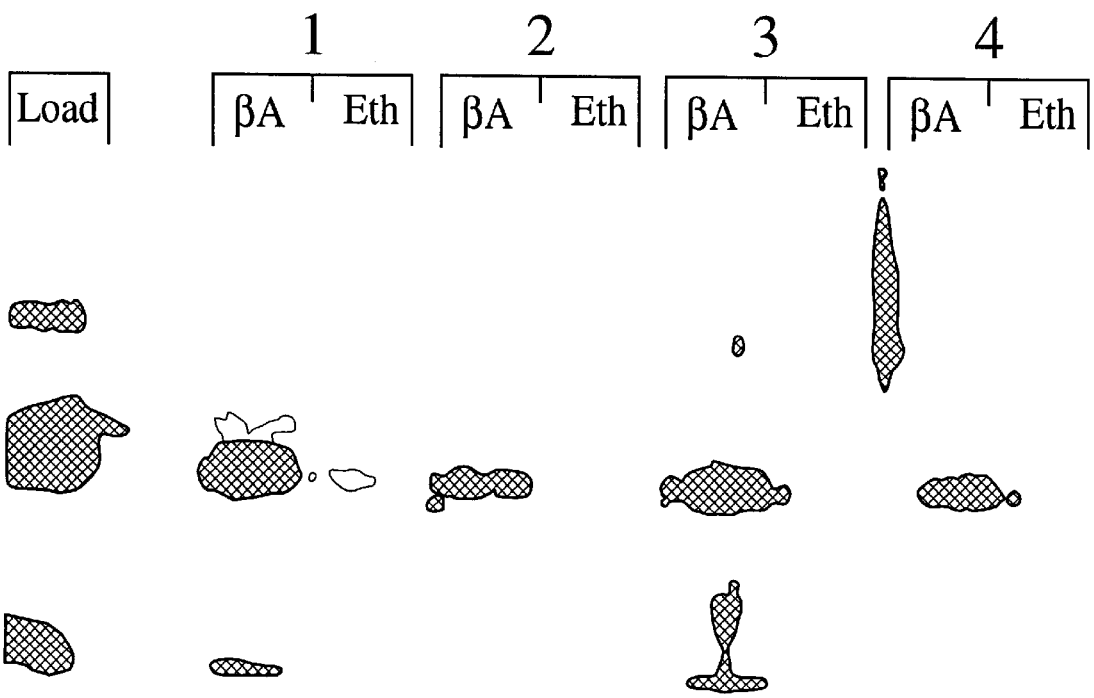

Results: Purified IgG was found to bind directly to βA$_{(1-28)}$ peptide, and binding required the hinge region of the heavy chain. As shown in FIG. 1, panel 1, purified IgG binds to immobilized βA$_{(1-28)}$ peptide, and does not bind to the ethanolamine-blocked control membrane. Various domains of the immunoglobulin molecule were examined for binding to immobilized βA peptide. Fab (Panels 2 and 4) and Fc (panel 3) did not bind to βA$_{(1-28)}$ peptide. F(ab)'$_2$, containing the hinge region of the heavy chain, bound to immobilized βA$_{(1-28)}$ peptide (Panel 5). To further characterize the avidity of βA peptide binding, F(ab)'$_2$ was incubated with immobilized βA$_{(1-28)}$ or with immobilized ethanolamine (FIG. 2A), washed with PBS (Lane 1), and then followed by 10% SDS (Lane 2), 4 M urea (Lane 3), or 6 M guanidine hydrochloride (Lane 4). The F(ab)'$_2$ that bound to βA$_{(1-28)}$ was not eluted by urea, and was only partially eluted by SDS or guanidine hydrochloride. Similar results were obtained with IgG in CSF, shown in FIG. 2B. Incubation of cerebrospinal fluid, which contains IgG, with immobilized βA$_{(1-28)}$ or with immobilized ethanolamine, and washed under the conditions shown in FIG. 2A, revealed that cerebrospinal fluid (CSF) IgG avidly bound βA$_{(1-28)}$. In a previous study, Pardridge et al. (1987), examined human cerebrospinal fluid for protein immunoreactive with an antibody against synthetic βA$_{(1-28)}$, and demonstrated that CSF IgG was identified by this antibody, suggesting either cross-reactivity or the presence of βA peptide on IgG.

Figure 3:
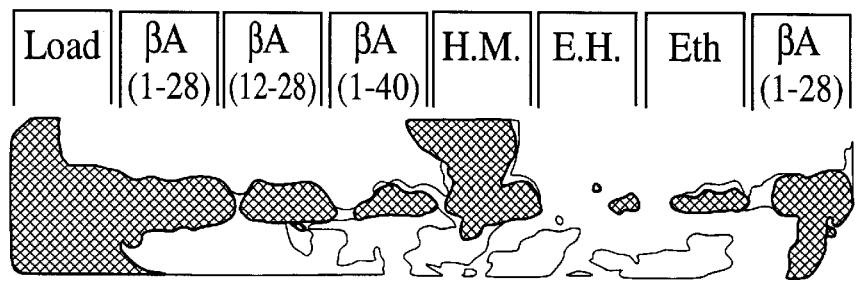
FIG. 3 shows binding of purified IgG to βA peptides and to other peptides. Affinity-purified IgG was incubated with $βA_{(1-28)}$, $βA_{(1-28)}$, $βA_{(1-40)}$, H.M. peptide, E.H. peptide, or ethanolamine, previously immobilized to Immobilon AV membrane discs. The membranes were then washed with PBS and 6M guanidine hydrochloride. Retained proteins were then eluted by boiling in Laemmli buffer, electrophoresed, and immunoglobulin visualized.

Both IgG and F(ab)'$_2$ bind with high avidity to full length βA peptide (βA$_{(1-40)}$). As illustrated in FIG. 3, affinity-purified IgG bound to βA$_{(1-40)}$, βA$_{(1-28)}$, and βA$_{(12-28)}$ Thus the binding requires amino acids 12–28 of βA. Peptide H.M. ("hydro-mimic" peptide) is a 17 amino acid peptide with a hydropathy profile similar to βA$_{(12-28)}$, but with different amino acids, while peptide E. H. ("evenhydro" peptide) is a 17 amino acid peptide containing the same amino acids as βA$_{(12-28)}$ but with a scrambled sequence (Strittmatter et al., *Proc. Natl. Acad. Sci.* 90, 1977 (1993)). IgG bound to peptide H.M. but only bound minimally to peptide E.H. FIG. 3. Similar results were obtained with purified F(ab)'$_2$ (data not shown). The lack of binding of IgG and F(ab)'$_2$ to the scrambled amino acid sequence of peptide E.H. suggests a certain degree of specificity of interaction. Since IgG and F(ab)'$_2$ bound to peptide H.M., which has the same hydropathic profile as βA$_{(12-28)}$, binding may require specific steric, hydrophobic, or charge interactions.

These studies show that IgG binds directly and avidly to βA peptide; that the hinge region of the heavy chain is required for binding; and that binding requires amino acids 12–28 of βA. With βA bound to the hinge domain, the antigen-binding portion of IgG remains free to interact with other antigens.

EXAMPLE 3

Binding of IgG-Antigen Pairs to βA Peptide

Studies examining the binding of IgG to both antigen and βA$_{(1-28)}$ were conducted by incubating 1.0 µl cerebrospinal fluid (which contains albumin) with either 0.5 mg sheep anti-human serum albumin (anti-HSA) antibody or sheep antiferritin antibody (control) in 150 µl PBS for thirty minutes at room temperature. The mixtures were then incubated 30 minutes with either immobilized βA$_{(1-28)}$ peptide or immobilized ethanolamine (control) at room temperature. The membranes were first washed with 3.0 ml PBS, followed by 1.0 ml 6 M guanidine hydrochloride, and 2.0 ml PBS. The retained proteins were then eluted by boiling five minutes in 150 µl Laemmli buffer. Proteins were then electrophoresed and transferred to Immobilon P membrane as described above.

The Western transfer membrane was incubated with peroxidase-conjugated sheep anti-HSA antibody (1:10,000 dilution in Blotto) overnight at 4° C. After washing the membranes as described above, immunolabeled albumin was visualized by chemoluminescence. All of the experiments shown in the FIGS. 4 and 5 have been replicated at least once (duplicate data not shown).

Figure 4:
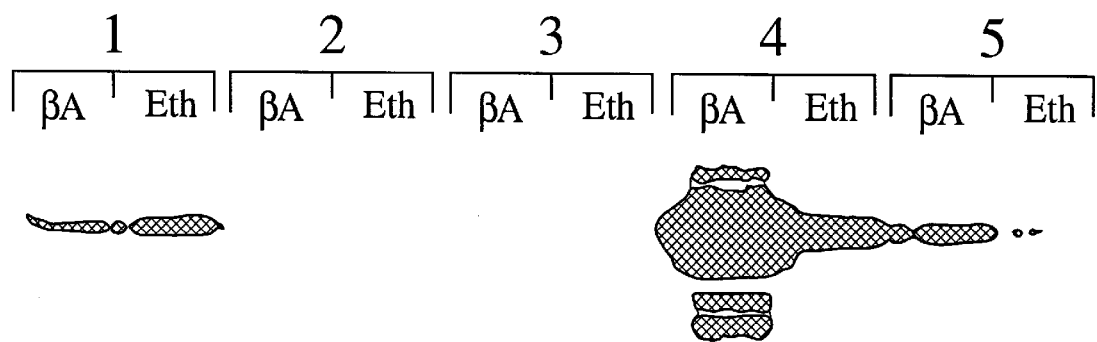
FIG. 4 shows binding of CSF albumin to immobilized βA, Panel 1); to immobilized $βA_{(1-28)}$ after preincubation; with anti-albumin IgG (Panel 4); and to immobilized $βA_{(1-28)}$ after preincubation with anti-ferritin IgG (Panel 5). Cerebrospinal fluid was incubated with immobilized βA or with immobilized ethanolamine (Eth). As controls, anti-albumin IgG alone (Panel 2) and anti-ferritin IgG alone (Panel 3)

To test whether IgG can deliver an antigen to the senile plaque by first binding its specific antigen and then binding to βA peptide, the ability of albumin to bind to βA peptide directly and to bind to βA peptide indirectly through anti-albumin IgG was examined. As shown in FIG. 4, panel 1, albumin in cerebrospinal fluid was weakly bound to both immobilized βA peptide or to ethanolamine-bound control membranes. Cerebrospinal fluid was then first incubated with either an anti-albumin IgG or with an anti-ferritin IgG (as a control) and was then incubated with immobilized βA peptide. Prior incubation with anti-albumin IgG markedly increased the amount of albumin bound to the immobilized βA peptide (FIG. 4, panel 4) in contrast to pre-incubation with the anti-ferritin IgG control (FIG. 4, panel 5). Neither of the antibodies were immunoreactive for albumin (FIG. 4, panels 2 and 3) and both antibodies bound equally well to immobilized βA peptide (data not shown).

These studies show that albumin, which binds weakly to βA peptide, can be targeted to βA peptide via IgG.

EXAMPLE 4

Binding of Antigen to IgG-βA Peptide Pairs

The following experiments indicate that IgG bound to βA$_{(1-28)}$ peptide can still recognize and bind antigen. Both anti-albumin IgG and anti-ferritin IgG were first bound to immobilized βA$_{(1-28)}$ peptide, and were then incubated with cerebrospinal fluid. The anti-albumin IgG continued to bind albumin (FIG. 5, lanes 2 and 5) while the anti-ferritin antibody did not (FIG. 5, Lane 3 and 6). The binding of albumin to βA peptide via specific IgG was maintained even after wash with 6 M guanidine hydrochloride (FIG. 5, Lane 5).

Data in FIGS. 4 and 5 indicate that IgG is capable of high avidity binding to antigen and to βA peptide simultaneously, and that the temporal sequence of interaction is not important.

The foregoing is illustrative of the present invention and is not to be construed as limiting thereof. The invention is defined by the following claims, with equivalents of the claims to be included therein.

That which is claimed is:

1. An in vitro method of binding a compound to β-amyloid peptide, comprising:

contacting an IgG linker antibody having an intact hinge region to β-amyloid peptide, wherein said linker antibody does not have a variable region that is specific for β-amyloid peptide, and wherein the presence of said intact hinge region is required for binding to β-amyloid peptide; and binding said compound to said antibody so that said compound is bound to β-amyloid peptide, wherein said compound is an antigenic compound, wherein said antibody includes a variable region which binds specifically to said antigenic compound, and wherein said binding step is carred out by binding said antigenic compound to said variable region.

2. The method according to claim 1, wherein said compound is a detectable group.

3. The method according to claim 1, wherein said compound is selected from the group consisting of radiolabels, enzyme labels, and fluorescent labels.

4. The method according to claim 1, wherein said binding step is carried out prior to said contacting step.

5. The method according to claim 1, wherein said binding step is carried out after said contacting step.

6. The method according to claim 1, wherein said binding step is carried out concurrently with said contacting step.

7. The method according to claim 1, wherein said β-amyloid peptide resides in nerve tissue and said contacting step is carried out in nerve tissue.

8. An in vitro method of binding an antigenic compound which is a detectable group to β-amyloid peptide, comprising:

contacting an IgG linker antibody having an intact hinge region and at least one variable region antigen binding site to β-amyloid peptide, wherein sad linker antibody is an antibody F(ab')$_2$ fragment, wherein said linker antibody does not have a variable region that is specific for β-amyloid peptide, and wherein the presence of said intact hinge region is required for binding to β-amyloid peptide; and binding said antgenic compound to said variable region so that said detectable group is bound to the β-amyloid peptide.

9. The method according to claim 8, wherein said binding step is carried out prior to said contacting step.

10. The method according to claim 8, wherein said binding step is carried out after said contacting step.

11. The method according to claim 8, wherein said binding step is carried out concurrently with said contacting step.

12. The method according to claim 8, wherein said β-amyloid peptide resides in nerve tissue and said contacting step is carried out in nerve tissue.

* * * * *